United States Patent [19]

Müller et al.

[11] Patent Number: 4,714,792

[45] Date of Patent: Dec. 22, 1987

[54] PROCESS FOR THE PRODUCTION OF 1,2,3-TRICHLOROPROPANE

[75] Inventors: Dieter J. Müller; Heinrich Wehmeyer, both of Marl, Fed. Rep. of Germany

[73] Assignee: Huels Aktiengesellschaft, Marl, Fed. Rep. of Germany

[21] Appl. No.: 773,168

[22] Filed: Sep. 6, 1985

[30] Foreign Application Priority Data

Sep. 6, 1984 [DE] Fed. Rep. of Germany ....... 3432720

[51] Int. Cl.$^4$ .............................................. C07C 17/06
[52] U.S. Cl. .................................................. 570/261
[58] Field of Search ........................................... 570/261

[56] References Cited

U.S. PATENT DOCUMENTS 3,338,982 8/1967 Leach et al. ........................ 570/247

FOREIGN PATENT DOCUMENTS 525654 7/1977 U.S.S.R. .............................. 570/253

Primary Examiner—Donald B. Moyer
Assistant Examiner—Joseph A. Boska
Attorney, Agent, or Firm—Millen & White

[57] ABSTRACT 1,2,3-trichloropropane is prepared by reacting allyl chloride with sulfuryl chloride, in the presence of 1-10,000 ppm of a nitrogen-containing base, a phosphine or a phosphine oxide. Suitable nitrogen-containing bases include aliphatic, aromatic and heterocyclic amines, and mixtures thereof; suitable phosphines are preferably aliphatic or aromatic phosphines and suitable phosphine oxides are aliphatic or aromatic phosphine oxides.

20 Claims, No Drawings

PROCESS FOR THE PRODUCTION OF 1,2,3-TRICHLOROPROPANE

CROSS-REFERENCE TO RELATED APPLICATIONS

This application is related to commonly assigned U.S. application Ser. Nos. 644,418 and 644,466, both of Aug. 27, 1984, and Ser. No. 727,176, of Apr. 25, 1985, and U.S. Pat. No. 4,587,367 which disclosures are incorporated by reference herein.

BACKGROUND OF THE INVENTION

This invention relates to a process for the production of 1,2,3-trichloropropane by reacting allyl chloride with sulfuryl chloride in the presence of a catalyst.

Chlorination of allyl chloride to 1,2,3-trichloropropane with sulfuryl chloride has been possible, according to the prior art only in the presence of catalytically effective amounts of peroxide compounds (JACS 61:2145 [1939]; JACS 61:3433 [1939]; U.S. Pat. No. 2,302,228). Such free radical chlorination, however, proceeds with low selectivity. Even when a fourfold excess of allyl chloride is used in such processes, when the total yields of chlorination products are 80%, only 37% of the product distribution consists of 1,2,3-trichloropropane (U.S. Pat. No. 2,302,228, Example 4). Higher yields are attainable only when the reaction mixture is diluted considerably with, for example, CCl$_4$ in a weight proportion of at least 1:1. Here, too, the reaction is possible only in the presence of peroxide compounds, and yields of 1,2,3-trichloropropane are 80-90% (JACS 61:3433 [1939]).

These methods are industrially unsatisfactory because they provide unacceptably low selectivity and/or an unacceptably low space-time yield.

SUMMARY OF THE INVENTION

Accordingly, it is an object of this invention to provide a process for producing 1,2,3-trichloropropane by the reaction of allyl chloride with sulfuryl chloride without any dilution being required, without superstoichiometric quantities of allyl chloride, and/or with high selectivity and a high space-time yield.

Upon further study of the specification and appended claims, further objects and advantages of this invention will become apparent to those skilled in the art.

These objects have been attained according to this invention by a process comprising reacting allyl chloride with sulfuryl chloride, in the presence of an effective amount of a reaction-compatible and catalytically effective nitrogen-containing base or a phosphine or phosphine oxide.

DETAILED DISCUSSION

It has been found, surprisingly, that the reaction of allyl chloride with sulfuryl chloride leads, even without dilution with inert solvents, and without extreme excesses of allyl chloride, to 1,2,3-trichloropropane with an unexpectedly high yield of 80-90% by conducting the reaction in the presence of a catalytically effective amount of amines and/or phosphines or phosphine oxides. This surprising reaction takes place apparently not by way of the aforementioned free radical procedure, but rather apparently by way of an ionic mechanism heretofore unknown, in accordance with the following empirical equation:

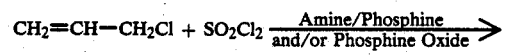

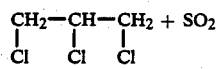

Thus, this invention does not involve free-radical-containing catalysts or catalysts forming free radicals under reaction conditions, e.g., the prior art peroxide catalysts or free-radical forming azo compounds, etc. The catalysts of this invention provide free pairs of electrons.

According to the invention, the reaction is conducted by chlorinating allyl chloride, preferably in the liquid phase, by the addition of SO$_2$Cl$_2$ in the presence of amines and/or phosphines or phosphine oxides at a temperature of from about 30° C. to about 70° C. The chlorination reaction proceeds exothermally with great speed so that it is expedient for a smooth performance of the reaction, to proceed by feeding metered quantities of sulfuryl chloride to the allyl chloride, with cooling of the reaction mixture after adding the amines or phosphines and heating to a starting temperature of about 30°-40° C. The rate at which the SO$_2$Cl$_2$ is fed to the allyl chloride preferably corresponds to the quantities being consumed by the reaction. Suitable reaction temperatures can approach the boiling temperature of the reaction mixture. It is also possible to operate under pressure to raise the reaction temperature. Suitable pressures include, for example, 1-3 bar. The heat of reaction can be removed via jacket cooling, as well as by way of vaporization/reflux cooling. As is shown by the reaction equation, the gaseous by-product SO$_2$ is formed from sulfuryl chloride. This by-product is continuously released in gaseous form and discharged.

Sulfuryl chloride and allyl chloride can be employed in a stoichiometric quantitative ratio for the reaction. Preferably, a quantity of SO$_2$Cl$_2$ that is less than stoichiometric (e.g., 70-95% thereof) will be used in this process since unreacted allyl chloride can be separated more easily from the resultant product mixture than unreacted sulfuryl chloride. After separation, unreacted allyl chloride can be reused. However, it is not deleterious for the reaction proper to utilize SO$_2$Cl$_2$ in stoichiometric excess.

The reaction can take place discontinuously, for example in an agitated vessel, as well as continuously, for example in a tubular reactor or in a cascade. The reaction is preferably performed in the liquid phase, the temperature and pressure of the system being chosen accordingly to generate liquid (or, if desired, gaseous) conditions.

Suitable catalysts for the chlorination reaction include primary, secondary and tertiary aliphatic amines (e.g., (mono-, di-, or tri-C$_{1-10}$-alkyl) amines), aromatic and heterocyclic amines or other nitrogen-containing bases, such as diisopropylamine, triethylamine, tributylamine, diphenylamine, benzidine or toluidines, pyridine, picolines, pyrrole, pyrazole, quinoline, carbazole or quinaldine. Also, other than the above-mentioned N-containing organic compounds may be useful such as amides like urea, substituted ureas or compounds such as hydrazines like diethylhydrazine or even hydrazones. Phosphines can also be used, such as aliphatic, primary, secondary or tertiary or aromatic, primary, secondary or tertiary phosphines, such as tributylphosphine and triphenylphosphine. Suitable phosphines include those corresponding to the amines listed above, the above listing being merely exemplary. Also usable are combinations of amines and/or phosphines. Phosphine oxides are also suitable, e.g., triphenylphosphine oxide and phosphine oxides corresponding to the phosphines above. Other P-containing organic compounds may be useful as catalysts such as P,P-dichlorophenylphosphine. Pyridine and/or tributylphosphine are preferred.

Normally, a concentration of 1–10,000 ppm of these compounds suffices for catalyzing the reaction. A concentration of 10–1,000 ppm is preferred. The desired reaction can still be carried out on allyl chloride having a low concentration of catalyst of about 1 ppm per this invention, but the reaction proceeds gradually and requires a longer initiation period. In the reaction of allyl chloride containing such a low concentration of a catalyst, it is difficult to control the course of the reaction although the reaction per se is still part of this invention. Accordingly, the reaction is preferably conducted with the addition of at least 10 ppm of a N-containing compound, phosphine or phosphine oxide, most preferably at least 50 ppm.

Since chlorinated hydrocarbons in many cases are commercially available already containing added amines as stabilizers, allyl chloride stabilized in this way may be reacted in accordance with this invention without requiring the introduction of an additional amine or phosphine.

The reaction generally proceeds under exclusion of light, at 30°–70° C., generally from normal pressure to about 1.5 bar, preferably at the boiling temperature of the reaction mixture which, at normal pressure, rises from initially about 42° C. to about 50° C.

The $SO_2Cl_2$ is generally metered into the reaction mixture during a period of about 3–15 minutes, and, in general, the total reaction time is about 60–120 minutes, as indicated by the cessation of released $SO_2$.

The resultant crude 1,2,3-trichloropropane is subjected to a standard fractionation, optimally after an optional water washing step and a drying step. The fractionation is preferably carried out under reduced pressure, since the product can partially decompose under thermal load. Pressure conditions for fractionation should be selected to enable separation of the desired product below 80° C.

The yields of 1,2,3-trichloropropane as predominant product in the process of this invention generally are greater than about 80%, e.g., range around 80–90%, based on converted allyl chloride, and the conversion of $SO_2Cl_2$, when used in less than stoichiometric amounts, is complete. The yields of 1,2,3-trichloropropane vary somewhat with the temperature regulation, the rate at which sulfuryl chloride is metered into the reaction mixture, the stoichiometric ratio of the reaction components, the choice of catalyst, and the reaction time.

A sulfonated product, the formation of which is enhanced by the effect of light, is the essential by-product. This undesired by-product can readily be separated by extractive methods using a water washing step.

A primary use of 1,2,3-trichloropropane is as intermediate for synthesis of derivatives of glycerole. Besides that 1,2,3-trichloropropane is used for a new synthesis of N,N-dimethylamino-1,3-dichloropropane (Chem. Abstr. 102(1):5639z).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

A temperature-controllable twin-jacket vessel with magnetic stirrer and reflux condenser is charged with 1 mole of allyl chloride, heated to the start-up temperature of 30° C. or, respectively, the reaction temperature, and, after addition of the catalyst, the allyl chloride is reacted with 0.8 mole of sulfuryl chloride under exclusion of light. The temperature in the reactor is maintained extensively constant by jacket and reflux cooling.

The sulfuryl chloride is fed in metered quantities by means of a pump uniformly within about 15 minutes, the introduction of $SO_2Cl_2$ taking place below the liquid level.

The gaseous $SO_2$ formed during the reaction escapes, in some cases together with some HCl, via the cooler and—if necessary—through a pressure-maintaining valve into a receiver with dilute sodium hydroxide solution.

After termination of the reaction, i.e. once evolution of gas has ceased, the reaction mixture is subjected, after cooling to 25° C., to a water washing step and drying with $CaCl_2$. The dried product mixture is analyzed by gas chromatography.

The results of this process experiment are set forth in Table 1.

TABLE 1

| Catalyst Feed | ppm | Reaction Temp. °C. | Reaction Time min | Amount of Product after Water Washing and Drying | Content of 1,2,3-Trichloropropane (without Excess Allyl Chloride) % | Yield % |
|---|---|---|---|---|---|---|
| Pyridine | 1,000 | 45 | 90 | 108 | 95.5 | 87 |
| Pyridine | 10 | 40 | 120 | 108 | 92.0 | 84 |
| Tributylamine | 100 | 45 | 90 | 107 | 93.5 | 85 |
| Diphenylamine | 100 | 50 | 90 | 104 | 91.5 | 81 |
| Tributylphosphine | 100 | 50 | 60 | 110 | 96.5 | 90 |
| Triphenylphosphine Oxide | 1,000 | 45 | 70 | 107 | 90.5 | 82 |
| — (*) | | 50–60 | 150 | 105 | 90.0 | 80 |

(*) The allyl chloride employed had an N content of about 1 ppm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of 1,2,3-trichloropropane as predominant product comprising reacting allyl chloride with sulfuryl chloride, in the presence of a catalytically effective amount of an aliphatic amine, an aromatic amine, a phosphine or a phosphine oxide.

2. A process of claim 1, wherein the reaction is conducted in the liquid phase.

3. A process of claim 1, wherein the reaction is conducted at 30°–7020 C.

4. A process of claim 1, wherein the reaction is conducted at the atmospheric boiling temperature of the reaction mixture.

5. A process of claim 1, wherein the amount of sulfuryl chloride used is less than the stoichiometric amount based on allyl chloride.

6. A process of claim 1, wherein the reaction is conducted substantially in the absence of light.

7. A process of claim 1, wherein the catalyst is an aliphatic amine.

8. A process of claim 1, wherein the catalyst is an aromatic amine.

9. A process of claim 1, wherein the catalyst is an aliphatic phosphine.

10. A process of claim 1, wherein the catalyst is an aromatic phosphine.

11. A process of claim 1, wherein the catalyst is an aliphatic phosphine oxide.

12. A process of claim 1, wherein the catalyst is an aromatic phosphine oxide.

13. A process of claim 1, wherein the catalyst is tributyl phosphine.

14. A process of claim 1, wherein the catalyst is present at a concentration of from 1–10,000 ppm.

15. A process of claim 1, wherein the catalyst is present at a concentration of from 10–10,000 ppm.

16. A process of claim 1, wherein the catalyst is present at a concentration of from 10–1,000 ppm.

17. A process of claim 1, wherein the reaction temperature is at the boiling point of the reaction mixture, the $SO_2Cl_2$ is metered into the reaction in 3–15 minutes and the total reaction time is 60–120 minutes.

18. A process of claim 1, further comprising fractionating the resultant product under reduced pressure.

19. A process of claim 1, further comprising separating sulfonated byproducts by a water washing step.

20. A process of claim 1 wherein the catalyst is tributyl phosphine.

* * * * *